United States Patent [19]

Hoekstra

[11] Patent Number: 4,663,464

[45] Date of Patent: May 5, 1987

[54] PROCESS FOR THE PREPARATION OF DIHYDRO-1H-PYRROLIZINE-3,5-(2H,6H)-DIONE

[75] Inventor: Marvin S. Hoekstra, Holland, Mich.

[73] Assignee: Warner-Lambert Company, Morris Plains, N.J.

[21] Appl. No.: 842,702

[22] Filed: Mar. 21, 1986

[51] Int. Cl.$^4$ .................... C07D 487/06; C07D 487/08
[52] U.S. Cl. ..................................... 548/453; 548/551
[58] Field of Search .......................................... 548/453

[56] References Cited

U.S. PATENT DOCUMENTS

| | | | |
|---|---|---|---|
| 4,372,966 | 2/1983 | Butler | 514/425 |
| 4,548,947 | 10/1985 | Butler et al. | 548/453 X |
| 4,563,469 | 1/1986 | Butler et al. | 548/453 X |
| 4,581,462 | 4/1986 | Yankee et al. | 548/453 |

OTHER PUBLICATIONS

Leonard, et al.; J. Am. Chem. Soc., 69, (1947), pp. 690–692.
Micheel, et al.; Chem. Ber., 88, (1955), pp. 509–510.
Micheel, et al.; Ann. Chem., 581, (1953), pp. 225–237.
Lukes et al., Coll. Czech. Cham. Comm., 12:278–279 (1947).

Primary Examiner—Joseph Paul Brust
Attorney, Agent, or Firm—Jerry F. Janssen

[57] ABSTRACT

Dihydro-1H-pyrrolizine-3,5-(2H,6H)-dione is produced in higher overall yield in a process which comprises catalytically hydrogenating a lower alkyl ester of 4-(hydroxyimino)heptanedioic acid in the presence of a tri-(lower alkyl)amine, followed by cyclization of the product thus produced in the presence of a cyclizing agent such as acetic anhydride.

4 Claims, No Drawings

PROCESS FOR THE PREPARATION OF DIHYDRO-1H-PYRROLIZINE-3,5-(2H,6H)-DIONE

BACKGROUND OF THE INVENTION

The present invention relates to chemical processes. More particularly, the present invention is concerned with an improved process for preparing dihydro-1H-pyrrolizine-3,5-(2H,6H)-dione.

Dihydro-1H-pyrrolizine-3,5-(2H,6H)-dione possesses useful pharmacological properties for enhancing memory and reversing the effects of amnesia caused by electroconvulsive shock. (See U.S. Pat. No. 4,372,966.)

The prior art discloses several alternative routes to dihydro-1H-pyrrolizine-3,5-(2H,6H)-dione starting with one or another derivative of heptanedioic acid, generally a 4-substituted-heptanedioic acid such as the 4-nitro, 4-amino-, 4-oxo-, or 4-hydroxyimino-derivative. However, most of these processes involve numerous steps or produce low overall yields of the desired end-product, typically on the order of 50% or less. Consequently, there is a need for an improved method of preparing this pharmacologically useful agent.

U.S. Pat. No. 4,372,966 to Butler discloses a method whereby dimethyl 4-nitro-heptanedioate is catalytically reduced by the action of hydrogen in the presence of palladium to produce a mixture of methyl 5-oxo-2-pyrrolidinepropanoate and the corresponding free acid. The mixture is next treated with base and then acidified to convert the ester in the mixture to the free acid. In a final step, the 5-oxo-2-pyrrolidinepropanoic is converted by the action of acetic anhydride to dihydro-1H-pyrrolizine-3,5-(2H,6H)-dione. The reported overall yield for this synthetic sequence is about 48%.

Lukes et al., *Coll. Czech. Chem. Comm.*, 12: 278-279 (1947) disclose a method by which diethyl 4-(hydroxyimino)heptanedioate is catalytically reduced by the action of platiunum oxide in the presence of ferrous chloride to produce a mixture of ethyl 5-oxo-2-pyrrolidinepropanoate and 4-oxo-heptanedioic acid. The yield of the pyrrolidine derivative is reported as 40%.

Leonard et al., *J. Am. Chem. Soc.*, 69: 690-692 (1947) disclose a method of preparing dihydro-1H-pyrrolizine-3,5-(2H,6H)-dione comprising catalytically reducing dimethyl 4-nitro-heptanedioate by the action of hydrogen in the presence of platinum oxide to methyl 5-oxo-2-pyrrolidinepropanoate in 55% yield. This material is subsequently cyclized in 60% yield to dihydro-1H-pyrrolizine-3,5-(2H,6H)-dione by heating for 30 hours under hydrogen at 250-300 atmospheres ($2.5 \times 10^4$–$3.0 \times 10^4$ kPascal) in the presence of copper chromite.

Micheel et al., *Ann. Chem.*, 581: 225-237 (1953) disclose the preparation of dihydro-1H-pyrrolizine3,5(2H,6H)-dione by first converting 4-aminoheptanedioic acid to the "half lactam" (i.e. 5-oxo-2-pyrrolidinepropanoic acid) and then cyclizing this material to the dione by the action of acetic anhydride.

Micheel et al., *Chem. Ber.*, 88: 509-510 (1955) dislcose a method of preparing dihydro-1H-pyrrolizine-3,5(2H,6H)-dione in 56% yield by the reduction of 4-oxo-heptanedioic acid, followed by the treatment of the 5-oxo-2-pyrrolidinepropanoic acid thus formed with acetyl chloride in acetic acid.

SUMMARY OF THE INVENTION

In accordance with the present invention an improved process for preparing dihydro-1H-pyrrolizine-3,5-(2H,6H)-dione comprises the steps of first catalytically hydrogenating a mono(lower alkyl) ester of 4-(hydroxyimino)heptanedioic acid in the presence of a tertiary lower alkyl amine to produce 5-oxo-2-pyrrolidinepropanoic acid, and thereafter heating the 5-oxo-2-pyrrolidinepropanoic acid in the presence of a cyclizing agent to form dihydro-1H-pyrrolizine-3,5-(2H,6H)-dione.

By "lower alkyl" as used throughout this specification and appended claims is meant branched or unbranched alkyl groups of one to three carbon atoms such as methyl, ethyl, propyl, and isopropyl.

The method of the present invention provides dihydro-1H-pyrrolizine-3,5(2H,6H)-dione in overall yields from the starting mono(lower alkyl) ester of 4-(hydroxyimino)heptanedioic acid which regularly exceed 80%, considerably higher than yields obtained from prior art methods. The improvements in the present method lie in the combined use of a mono(lower alkyl)ester of 4-(hydroxyimino)heptanedioic acid, and the catalytic hydrogenation in the presence of a tertiary amine.

The use of a mono-ester yields the free acid, 5-oxo-2-pyrrolidinepropanoic acid, directly without the need for a hydrolysis step as is required when the starting material is a diester such as taught by Lukes et al. (see above). Any lower alkyl monoester of 4-(hydroxyimino)heptanedioic acid may be employed in this step of the process, such as the monomethyl, monoethyl, monopropyl ester, and the like.

Following the step of reducing the starting hydroxyimino compound to 5-oxo-2-pyrrolidinepropanoic acid, the acid is cyclized to the desired final product, dihydro-1H-pyrrolizine-3,5(2H,6H)-dione, by heating the acid in the presence of a cyclizing agent such as as acid anhydride, 2,2,6-trimethyl-1,3-dioxen-4-one (TKD), or diketene. Preferred cyclizing agents for this step of the process include acid anhydrides, with acetic anhydride being most preferred.

Referring to the accompanying Reaction Scheme, the starting material, 4-(hydroxyimino)heptanedioic acid, monoalkyl ester, is prepared from the alkali metal salt of the monoalkyl ester, 2. This ester-salt, 2, is readily prepared by treatment of the spirodilactone 1 with any suitable lower alcohol in the presence of a base such as sodium carbonate, potassium carbonate and the like. The preparation of the spirodilactone 1 and its conversion to the alkali metal salt monoester 2 are disclosed by Pariza et al., *Synthetic Communications*, 13(3): 243–254 (1983). Preferred alcohols for this conversion are methyl and ethyl alcohol on the basis of cost, with methyl alcohol being most preferred.

The alkali metal salt 2 is converted to 4-(hydroxyimino)heptanedioic acid, monoalkyl ester 3 in high yield by heating the salt 2 in aqueous solution at temperatures between about 20°–50° C. with hydroxylamine hydrochloride for a period of from about 15 minutes to about one hour.

The principle contribution of the process of the present invention to improved yields of dihydro-1H-pyrrolizine-3,5(2H,6H)-dione lies in the next step indicated in the Reaction Scheme where the hydroxyimino monoester 3 is catalytically hydrogenated to produce 5-oxo-2-pyrrolidinepropanoic acid 4.

Reaction Scheme

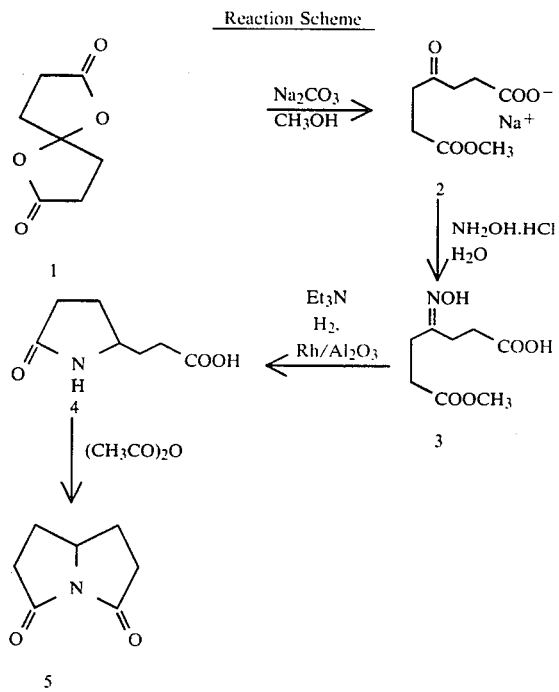

As can be seen by Example 1 below, when the reduction of 3 is carried out over rhodium/alumina catalyst in the presence of a tertiary lower alkyl amine such as triethylamine, in accordance with the method of this invention, very high yields of 5-oxo-2-pyrrolidinepropanoic acid are realized, with the product being substantially free of contaminating starting material.

These results are to be contrasted with those in Example 2 where the same reduction in the absence of a tertiary lower alkyl amine yielded a roughly 3:1 molar ratio of 5-oxo-2-pyrrolidinepropanoic acid and the corresponding methyl ester. This mixed material must be subjected to the further step of hydrolyzing the ester contained in the mixture in order to obtain the acid prior to the subsequent step of cyclizing to the desired end-product, dihydro-1H-pyrrolizine-3,5(2H,6H)-dione.

Further, as can be seen by reference to Example 3, catalytic reduction of an alkali metal salt of 4-(hydroxyimino)heptanedioic acid results in yields of the desired intermediate, 5-oxo-2-pyrrolidinepropanoic acid but in yields of only about 70%.

The following examples are provided to enable one skilled in the art to practice the present invention. These examples a illustrative of the process of this invention and are not to be read as limiting the scope of the invention as it is defined by the appended claims.

EXAMPLE 1

Catalytic Reduction of 4-(Hydroxyimino)heptanedioic Acid, Methyl Ester in the Presence of Triethylamine Preparation of 4-(Hydroximino)heptanedioic Acid, Monomethyl ester To a solution of 114.3 g (0.45 mol) of the crude sodium salt of 4-oxoheptanedioic acid, monomethyl ester (containing about 17% mixed carbonates of sodium ) in 400 ml of water was gradually added a solution of 36.9 g (0.53 mol) of hydroxylamine hydrochloride in 45 ml of water.

The mixture was warmed to 40° C. for 15 minutes, then cooled to 0°–5° C. while the pH was adjusted to 3.0 with 37% hydrochloric acid. The product was extracted four times with 250-ml portions of ethyl acetate. The organic layer was separated and dried over magnesium sulfate. The mixture was filtered and the solvent removed to yield 83.6 g (91%) of white crystalline 4-(hydroximino)heptanedioic acid, monomethyl ester mp 89°–91° C., which was found to be 98.9% pure by high pressure liquid chromatographic (HPLC) analysis.

Reduction of 4-(Hydroximino)heptanedioic acid, Monomethyl Ester

Monomethyl 4-(hydroxyimino)heptanedioate (15.7 g, 0.077 mol) was placed in a 500-ml hydrogenation bottle together with 300 ml of isopropyl alcohol, 7.8 g of triethylamine, and 2.27 g of 5% rhodium/alumina catalyst. The mixture was shaken for 16 hours under a hydrogen atmosphere at 50 psig (345 kPascal) while being heated at a temperature of 60° C.

At the end of this period, the catalyst was removed by filtration and the solvent and amine was removed under vacuum to yield 12.2 g (0.077 mol, 100%) of 5-oxo-2-pyrrolidinepropanoic acid.

EXAMPLE 2

Catalytic Reduction of 4-(Hydroxyimino)heptanedioic Acid, Methyl Ester in the Absence of Amine Monomethyl 4-(hydroxyimino)heptanedioate (16.7 g, 0.082 mol) was placed in a 500-ml hydrogenation bottle together with 300 ml of methyl alcohol and 2.4 g of 5% rhodium/alumina catalyst. The mixture was shaken for 16 hours under a hydrogen atmosphere at 50 psig (345 kPascal) while being heated at a temperature of 60° C.

The catalyst was removed by filtration under nitrogen, and the filter cake was washed with 50 ml of methanol. The solvent was removed from the filtrate under vacuum to yield a colorless oil. This material was heated at 90° C. for 9 hours under a vacuum of 3 Torr (0.4 kPascal) to remove any remaining solvent.

A sample of this material was analyzed by nuclear magnetic resonance spectroscopy which showed the presence of methyl ester in the material, indicating incomplete cyclization of the starting ester to 5-oxo-2-pyrrolidinepropanoic acid.

The material was heated at 110° C. for an additional 5 hours under a vacuum of 3 Torr (0.4 kPascal). Upon cooling, there was obtained 9.5 g of a solid product which showed by nuclear magnetic resonance spectroscopy to be a roughly 3:1 molar ratio of 5-oxo-2-pyrrolidinepropanoic acid and methyl 5-oxo-2-pyrrolidinepropanoate.

EXAMPLE 3

Catalytic Reduction of Sodium 4-(Hydroxyimino)heptanedioate in the Absence of Amine Sodium 4-(hydroxyimino)heptanedioate (11.9 g, 0.052 mol) was placed in a 500-ml hydrogenation bottle together with 285 ml of methyl alcohol and 2.2 g of 5% rhodium/alumina catalyst. The mixture was shaken for 1 hour under a hydrogen atmosphere at 50 psig (345 kPascal) at 60° C. after which time the uptake of hydrogen ceased at 30% of the theoretical amount. The catalyst was removed by filtration and replaced with 2.2 g of fresh 5% rhodium/alumina catalyst was added. Hydrogenation at 50 psig (345 kPascal) and 60° C. was continued for an additional 24 hours at which point the theoretical amount of hydrogen had been consumed.

The solvent was removed by filtration under nitrogen and the filter cake was washed with 50 ml of methanol. The solvent was removed from the filtrate under vacuum to yield 12.1 g of a semi-solid residue. This material was acidified with aqueous hydrochloric acid. Analysis of the material by high pressure liquid chromatographic (HPLC) methods indicated it to contain 68.8% 5-oxo-2-pyrrolidinepropanoic acid, 17.6% methyl 5-oxo-2-pyrrolidinepropanoate.

EXAMPLE 4

Cyclization of 5-Oxo-2-pyrrolidinepropanoic Acid to dihydro-1H-pyrrolizine-3,5-(2H,6H)-dione 5-Oxo-2-pyrrolidinepropanoic acid (15.7 g, 0.1 mol) was added to 45 ml of acetic anhydride and the mixture was heated slowly to 90° C. and held at that temperature for six hours. The mixture was cooled and the volatile materials stripped off at a temperature of 60° C. under vacuum. The residue (14.2 g) was dissolved in 230 ml of isopropyl alcohol, the solution decolorized, filtered, and concentrated to 30 ml. This solution was cooled 0°-5° C. for two hours, and the solid which separated was collected by filtration, washed twice with 25-ml portions of isopropyl alcohol to yield 12.5 g (89.9%) of dihydro-1H-pyrrolizine-3,5-( 2H,6H)-dione, mp 180.2°-181.8° C. which was found to be 99.5% pure by high pressure liquid chromatographic (HPLC) analysis.

I claim:

1. In a process for preparing dihydro-1H-pyrrolizine-3,5(2H, 6H)-dione comprising the steps of catalytically hydrogenating an ester of 4-(hydroxyimino)heptanedioic acid and subsequently cyclizing the resulting product to dihydro-1H-pyrrolizine- 3,5(2H,6H)-dione, the improvement comprises reacting an alcoholic solution of a mono(lower alkyl) ester of 4-(hydroxyimino)heptanedioic acid, wherein lower alkyl comprises from one to three carbon atoms, with hydrogen gas at a temperature of about 60° C. in the presence of rhodium/alumina catalyst and a tertiary lower alkyl amine, wherein said lower alkyl amine comprises from three to nine carbon atoms, to produce 5-oxo-2-pyrrolidinepropanoic acid; and thereafter heating said 5-oxo-2-pyrrolidinepropanoic acid in the presence of a cyclizing agent selected from acetic anhydride, 2,2,6-trimethyl-1,3-dioxen-4-one, and diketene at a temperature of about 90° C. to produce dihydro-1H-pyrrolizine-3,5(2H,6H)-dione.

2. The process as defined in claim 1 wherein said tertiary lower alkyl amine is triethyl amine.

3. The process as defined in claim 1 wherein said cyclizing agent is acetic anhydride.

4. The process as defined in claim 2 wherein said mono-(lower alkyl) ester of heptanedioic acid is monomethyl heptanedioate.

* * * * *